United States Patent
Tabuteau

(10) Patent No.: US 12,064,411 B1
(45) Date of Patent: *Aug. 20, 2024

(54) METHODS OF ADMINISTERING SOLRIAMFETOL TO LACTATING WOMEN

(71) Applicant: Axsome Malta Ltd., Qormi (MT)

(72) Inventor: Herriot Tabuteau, New York, NY (US)

(73) Assignee: AXSOME MALTA LTD., Qormi (MT)

( * ) Notice: Subject to any disclaimer, the term of this patent is extended or adjusted under 35 U.S.C. 154(b) by 0 days.

This patent is subject to a terminal disclaimer.

(21) Appl. No.: 18/323,229

(22) Filed: May 24, 2023

Related U.S. Application Data

(63) Continuation of application No. 18/148,682, filed on Dec. 30, 2022, now Pat. No. 11,771,666.

(51) Int. Cl.
*A61K 31/27* (2006.01)
*A61K 9/00* (2006.01)
*A61P 43/00* (2006.01)

(52) U.S. Cl.
CPC ............ *A61K 31/27* (2013.01); *A61K 9/0053* (2013.01); *A61P 43/00* (2018.01)

(58) Field of Classification Search
CPC ................................ A61K 31/27; A61P 43/00
See application file for complete search history.

(56) References Cited

U.S. PATENT DOCUMENTS

| | | | | |
|---|---|---|---|---|
| 10,912,754 | B2 * | 2/2021 | Carter | A61K 9/48 |
| 11,771,666 | B1 * | 10/2023 | Tabuteau | A61K 31/27 514/534 |
| 11,771,667 | B1 * | 10/2023 | Tabuteau | A61K 31/27 514/534 |
| 11,779,554 | B1 * | 10/2023 | Tabuteau | A61K 9/0053 514/534 |
| 11,793,776 | B1 * | 10/2023 | Tabuteau | A61K 31/165 |
| 11,872,203 | B1 * | 1/2024 | Tabuteau | A61K 31/165 |
| 11,872,204 | B1 * | 1/2024 | Tabuteau | A61K 31/165 |

OTHER PUBLICATIONS

Drugs.com. "Solriamfetol use while Breastfeeding." Drugs.com [Internet]. [Updated: Mar. 15, 2023]. Available from: https://www.drugs.com/breastfeeding/solriamfetol.html#infants. 2 pages. (Year: 2023).*
Gardiner et al. "Drug Safety in Lactation." (May 2001) https://www.medsafe.govt.nz/profs/puarticles/lactation.htm. 11 pages. (Year: 2001).*
Norgend, H. "Drug use and breastfeeding 1089-93." Tidsskr Nor Legeforen nr. 9, 2012; 132: 1089—93 https://tidsskriftet.no/en/2012/05/drug-use-and-breastfeeding. (Year: 2012).*
"Sunosi Medication Guide", FDA, Mar. 2019.
Banta-Wright, Sandra A, "Minimizing Infant Exposure to and Risks from Medications while Breastfeeding", J of Perinatal & Neonatal Nursing, Sep. 1997, 112(2), p. 71-84.
FDA , "Clinical Lactation Studies: Considerations for Study Design Guidance for Industry", FDA Guidance Document, May 2019, (13 pages).
Flygare, Julie , "New Research for Breastfeeding Mothers with Narcolepsy", https://julieflygare.com/new-research-for-breastfeeding-mothers-with-narcolepsy (2018).
"U.S. Appl. No. 18/148,682; Office Action mailed Apr. 19, 2023".
"U.S. Appl. No. 18/176,816; Office Action mailed May 17, 2023".
"U.S. Appl. No. 18/176,860; Office Action mailed May 17, 2023".
U.S. Appl. No. 18/323,232; Office Action mailed Aug. 17, 2023.
U.S. Appl. No. 18/323,236; office action mailed Aug. 31, 2023.
Barker et al. "Living with Narcolepsy: Current Management Strategies, Future Prospects, and Overlooked Real-Life Concerns" Nature and Science of Sleep, 12:453-466 (2020).

* cited by examiner

*Primary Examiner* — Jeffrey S Lundgren
*Assistant Examiner* — Chris E Simmons
(74) *Attorney, Agent, or Firm* — HUESCHEN AND SAGE

(57) ABSTRACT

Provided herein according to some embodiments is a method for decreasing the potential for adverse events from solriamfetol in an infant fed breast milk obtained from a subject treated with solriamfetol comprising: orally administering the solriamfetol to the subject at a daily dose of about 37.5 mg to about 300 mg; and feeding the infant breast milk from the subject at least about 5 hours after administering the solriamfetol to the subject, thereby decreasing potential for adverse events from solriamfetol in an infant.

18 Claims, 2 Drawing Sheets

METHODS OF ADMINISTERING SOLRIAMFETOL TO LACTATING WOMEN

STATEMENT OF PRIORITY

This application is a continuation of and claims priority to U.S. application Ser. No. 18/148,682 filed Dec. 30, 2022.

FIELD OF THE INVENTION

The present invention relates to methods of administering solriamfetol to a lactating subject while reducing the potential for adverse events from solriamfetol in an infant fed breast milk from the subject.

BACKGROUND OF THE INVENTION

Solriamfetol is a selective dopamine and norepinephrine reuptake inhibitor that has received marketing approval in the US for improving wakefulness in adult subjects with excessive daytime sleepiness (EDS) associated with narcolepsy or obstructive sleep apnea (OSA). Solriamfetol has been demonstrated to be useful in the treatment of a variety of disorders, including excessive daytime sleepiness, cataplexy, narcolepsy, fatigue, depression, bipolar disorder, fibromyalgia, and others.

Pharmacokinetic studies have demonstrated rapid absorption and high oral bioavailability of solriamfetol with dose-proportional exposure (maximum serum concentration and area under the concentration-time curve [AUC]) in animals tested.

The present invention overcomes shortcomings in the art by providing methods of administering solriamfetol to a lactating subject while reducing the potential for adverse events from solriamfetol in an infant fed breast milk from the subject.

SUMMARY OF THE INVENTION

The present invention relates to the development of methods of reducing the potential for adverse events from solriamfetol in an infant fed breast milk from the subject. The invention additionally related to a method of reducing exposure to solriamfetol in an infant fed breast milk obtained from a subject treated with solriamfetol.

Accordingly, one aspect of the invention relates to a method of reducing exposure to solriamfetol in an infant fed breast milk obtained from a subject treated with solriamfetol comprising: orally administering the solriamfetol to the subject at a daily dose of about 37.5 mg to about 300 mg; and feeding the infant breast milk from the subject at least about 5 hours after administering the solriamfetol to the subject, thereby reducing exposure to solriamfetol in the infant.

Another aspect of the invention relates to a method for decreasing the potential for adverse events from solriamfetol in an infant fed breast milk obtained from a subject treated with solriamfetol comprising: administering solriamfetol orally at a daily dose of between 37.5 mg and 300 mg to the subject; and feeding the infant breast milk from the subject at least about 5 hours after administering the solriamfetol to the subject, thereby decreasing the potential for adverse events from solriamfetol in the infant. In some embodiments, the daily dose of solriamfetol is 150 mg.

An aspect of the invention relates to a method treating a disorder treatable with solriamfetol in a subject producing breast milk for feeding an infant, comprising: administering solriamfetol orally at a daily dose of between 37.5 mg and 300 mg to the subject; and reducing exposure to solriamfetol and/or decreasing the potential for adverse events in the infant fed breast milk from the subject comprising feeding the infant breast milk from the subject at least about 5 hours after administering the solriamfetol to the subject. The disorder treatable with solriamfetol can be, without limitation, narcolepsy, excessive daytime sleepiness, obstructive sleep apnea, attention deficit/hyperactivity disorder, cognitive impairment or binge eating disorder.

In some embodiments, the method provides a daily infant dose of solriamfetol of about 0.3 mg or lower. In some embodiments, the method achieves a relative infant dose of less than about 9% of the subject weight-adjusted dose. In some embodiments, the method achieves a relative infant dose of less than about 5% of the subject weight-adjusted dose.

In some embodiments, the infant does not experience agitation, insomnia, anorexia, or reduced weight gain due to solriamfetol exposure.

In some embodiments, the subject is from 1 day to 24 months postpartum or from 10 days to 12 months postpartum.

In some embodiments, the subject is being treated with solriamfetol for narcolepsy, excessive daytime sleepiness, obstructive sleep apnea, attention deficit/hyperactivity disorder, cognitive impairment, or binge eating disorder.

In some embodiments, the subject is a woman between the ages of 18 and 45 years.

In some embodiments, the adverse events are one or more of agitation, insomnia, anorexia, or reduced weight gain.

Methods of treating a disorder amenable to treatment with solriamfetol in a subject who is breastfeeding an infant are provided comprising orally administering solriamfetol at a daily dose of between about 37.5 mg and 300 mg to the subject.

These and other aspects of the invention are set forth in more detail in the description of the invention below.

DETAILED DESCRIPTION

Figure 1:
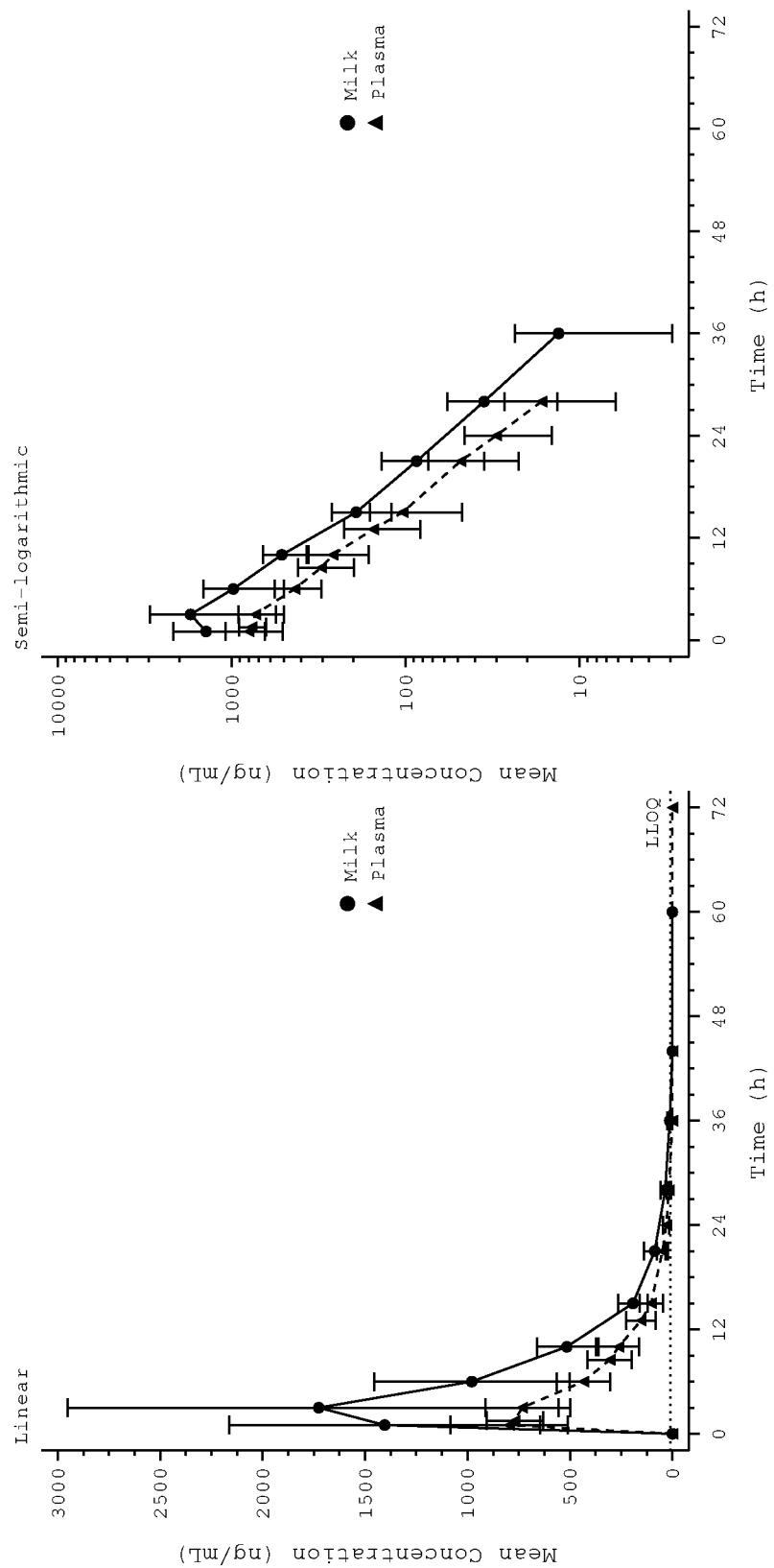
FIG. 1. Time course of mean solriamfetol breast milk and plasma concentration-time profiles on linear and semi-logarithmic scales.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In addition, any references cited herein are incorporated by reference in their entireties.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Pharmaceutically acceptable carrier" (sometimes referred to as a "carrier") refers to a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold and/or can be expressed in the enhancement and/or increase of a specified level and/or activity of at least about 1%, 5%, 10%, 15%, 25%, 35%, 40%, 50%, 60%, 75%, 80%, 90%, 95% or more.

"Inhibit" or "reduce" or grammatical variations thereof as used herein refers to a decrease or diminishment in the specified level or activity of at least about 1, 5, 10, 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

"Treat," "treating" and similar terms as used herein in the context of treating a subject refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, syndrome, or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur, delay the onset of the disease, or to reduce the severity of the disease should it occur. The subject may have been identified as being at risk of developing the disease (e.g., at increased risk relative to the general population or as having a risk factor that increases the likelihood of developing the disease.

Grammatical variations of "administer," "administration," and "administering" to a subject include any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration," "administration in combination," "simultaneous administration," or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g., greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's Pharmaceutical Science; 21st ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

"Bioavailability," as used herein, refers to the estimated area under the curve, or AUC of the active drug in systemic circulation after oral administration with a dosage form as disclosed herein when compared with the AUC of the active drug in systemic circulation after intravenous administration of the active drug. The AUC is affected by the extent to which the drug is absorbed in the GI tract.

Products are considered to be "bioequivalent" if the relative mean $C_{max}$, $AUC_{(0-t)}$ and $AUC_{(0-\infty)}$ of the test product to reference product is within 80% to 125%.

The term "$AUC_{(0-t)}$" means the area under the plasma concentration curve from time 0 to time t.

The term "$AUC_{(0-\infty)}$" or "$AUC_{0-inf}$" means the area under the plasma concentration time curve from time 0 to infinity.

"$C_{max}$" refers to the maximum milk or plasma concentration of solriamfetol.

"$T_{max}$" refers to the time to maximum milk or plasma concentration for a given drug.

"$t_{1/2}$" refers to the time to reduce the milk and plasma concentration by 50% during the terminal elimination phase of the drug.

Milk:plasma ratio means AUC in breast milk divided by AUC in plasma.

"$A_{milk}$" means the amount excreted in breast milk over 72 hours.

"Vd/F" means the apparent volume of distribution in plasma.

"CL/F" is the apparent oral clearance in plasma.

AUC0-t is the area under the concentration-time curve from time 0 to the time t of the last quantifiable concentration (milk and plasma).

The present invention is based, in part, on methods of using Sunosi® (referred to herein as solriamfetol (also known as (R)-2-amino-3-phenylpropyl carbamate (APC), and previously known as JZP-110, ADX-N05, R228060, and YKP10A)) in lactating subjects with a disorder amenable to treatment with solriamfetol while reducing the potential for adverse effects in infants fed the subject's breast milk. Administration of solriamfetol to subjects expressing breast milk presents challenges. In a nonclinical study in rats, solriamfetol was detected in breast milk, with solriamfetol milk concentrations higher than solriamfetol plasma concentrations. It is desirable to reduce or minimize any adverse effects from the daily dose received by an infant fed breast milk from a subject treated with solriamfetol. In addition, it is desirable to identify methods that allow for the safety and tolerability of solriamfetol in nursing subjects.

Accordingly, one aspect of the invention relates to a method of reducing exposure to solriamfetol in an infant fed breast milk obtained from a subject treated with solriamfetol comprising orally administering the solriamfetol to the subject at a daily dose of about 37.5 mg to about 300 mg; and feeding the infant breast milk from the subject at least about 5 hours after administering the solriamfetol to the subject, thereby reducing exposure to solriamfetol in the infant.

One aspect of the invention comprises methods for decreasing the potential for adverse events from solriamfetol in an infant fed breast milk obtained from a subject treated with solriamfetol comprising administering solriamfetol orally at a daily dose of between 37.5 mg and 300 mg to the subject; and feeding the infant breast milk from the subject at least about 5 hours after administering the solriamfetol to the subject, thereby decreasing the potential for adverse events from solriamfetol in the infant. In an embodiment, the adverse event is one or more of agitation, insomnia, anorexia, or reduced weight gain.

One aspect of the invention relates to a method for treating a disorder treatable with solriamfetol in a subject producing breast milk for feeding an infant, comprising administering solriamfetol orally at a daily dose of between 37.5 mg and 300 mg to the subject; and reducing exposure to solriamfetol and/or decreasing the potential for adverse events in the infant fed breast milk from the subject, comprising feeding the infant breast milk obtained from the subject at least about 5 hours after administering the solriamfetol to the subject. In one embodiment, the method reduces solriamfetol in the infant and the infant does not experience agitation, insomnia, anorexia, or reduced weight gain due to solriamfetol exposure. In one embodiment, the adverse events are one or more of agitation, insomnia, anorexia, or reduced weight gain.

A "disorder amenable to treatment with solriamfetol" or a "disorder treatable with solriamfetol" refers to any disorder in which administration of solriamfetol to a subject results in the treatment of one or more symptoms of the disorder in the subject. Example disorders amenable to treatment with solriamfetol include narcolepsy, cataplexy, excessive daytime sleepiness, obstructive sleep apnea, drug addiction, sexual dysfunction, fatigue, fibromyalgia, attention deficit/hyperactivity disorder (ADHD), cognitive impairment and/or cognitive dysfunction, restless legs syndrome, depression, bipolar disorder, obesity, or binge eating disorder. In some embodiments, the disorders amenable to treatment with solriamfetol include narcolepsy, excessive daytime sleepiness, obstructive sleep apnea, cognitive impairment, attention deficit/hyperactivity disorder, or binge eating disorder. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. All of the above patents and applications are hereby incorporated by reference in their entireties for all purposes.

"Excessive daytime sleepiness" or "EDS" refers to persistent sleepiness at a time when the individual would be expected to be awake and alert, even during the day after apparently adequate or even prolonged nighttime sleep. EDS may be the result of a sleep disorder or a symptom of another underlying disorder such as narcolepsy, sleep apnea, circadian rhythm sleep disorder, or idiopathic hypersomnia. While the name includes "daytime," it is understood that the sleepiness may occur at other times that the subject should be awake, such as nighttime or other times, e.g., if the subject is working nightshift. It is also understood that EDS is medically distinct from fatigue and disorders associated with fatigue.

In some embodiments, the cause of the EDS may be, without limitation, central nervous system (CNS) pathologic abnormalities, stroke, narcolepsy, idiopathic CNS hypersomnia; sleep deficiency, sleep apnea, obstructive sleep apnea, insufficient nocturnal sleep, chronic pain, acute pain, Parkinson's disease, urinary incontinence, multiple sclerosis fatigue, attention deficit hyperactivity disorder (ADHD), Alzheimer's disorder, major depression, bipolar disorder, cardiac ischemia; misalignments of the body's circadian pacemaker with the environment, jet lag, shift work, or sedating drugs.

In certain embodiments, solriamfetol structure is given below as formula I:

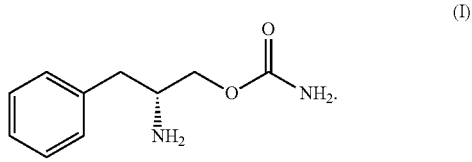 [SMILES: NC(=O)OC[C@H](N)Cc1ccccc1]

(I)

Methods for producing solriamfetol and related compounds can be found in U.S. Pat. Nos. 10,829,443, 5,955,499; 5,705,640; 6,140,532 and 5,756,817. All of the above patents and applications are hereby incorporated by reference in their entireties for all purposes.

In one embodiment, the methods detailed herein provide an infant fed breast milk from a subject to whom solriamfetol is administered does not experience adverse events, e.g., agitation, insomnia, anorexia, or reduced weight gain due to solriamfetol exposure. Monitoring the infant for agitation, insomnia, anorexia, or reduced weight gain can be performed. For example, monitoring and/or detecting weight loss, reduced weight gain, reduction in number of feedings or lessened intake, reduction in volume of milk ingested can be performed. Monitoring increase in agitation and/or insomnia in the infant, including a reduction of sleeping hours and/or time to fall asleep and stay asleep can also be performed to identify changes in the infant. In some embodiments, the monitoring for changes in the infant is performed at 3 or more hours subsequent to administering of the solriamfetol dose and subsequent to initiation of infant feeding with breast milk from the subject, for example at 3 hours, 4, hours, 5 hours, 6 hours, 7 hours, 8 hours, 9 hours, 10 hours or more subsequent to administering of the solriamfetol dose. Monitoring for any changes experienced by the infant (e.g., agitation, insomnia, anorexia, or reduced weight gain) can be performed over the time period in which solriamfetol is administered to the subject, which may be over days, weeks, or months, with monitoring over any interval in that time frame, including hourly, daily, weekly, monthly or any time range therein.

In one embodiment, the method provides a daily infant dose of solriamfetol of about 0.3 mg or lower, e.g., about 0.29 mg, about 0.28 mg, about 0.27 mg, about 0.26 mg, about 0.25 mg, about 0.24 mg, about 0.23 mg, about 0.22 mg, about 0.21 mg, about 0.20 mg, about 0.19 mg, about 0.18 mg, about 0.17 mg, about 0.16 mg, about 0.15 mg, or lower. The daily infant dose means the daily dose that was received by the infant through feeding of breast milk.

In some embodiments, breast milk for feeding of the infant is expressed or produced from the subject at 3 or more hours, 4 or more hours, or 5 or more hours, for example at 3 hours, 4, hours, 5 hours, 6 hours, 7 hours, 8 hours, 9 hours, 10 hours or more, subsequent to administering of the solriamfetol dose to the subject. In some embodiments, the breast milk produced from the subject for infant feeding in the methods detailed herein occurs at about the mean elimination half-life of solriamfetol or later, i.e., at about 5 hours, subsequent to administration of the solriamfetol. In some embodiments, the breastfeeding of the infant is performed at 3 or more hours, 4 or more hours, or 5 or more hours subsequent to administering of the solriamfetol dose to the subject. In some embodiments, the breast milk for feeding the infant is obtained from the subject at 3 or more hours, 4 or more hours, or 5 or more hours subsequent to administering of the solriamfetol dose to the subject.

In some embodiments, the method achieves a relative infant dose, the percentage of the weight-adjusted subject dose excreted in breast milk over 24 hours, of less than about 10%, less than about 9.5%, less than about 9%, less than about 8.5%, less than about 8%, less than about 7.5%, less than about 7%, less than about 6.5%, less than about 6%, less than about 5.5%, less than about 5%, less than about 4.9%, less than about 4.8%, less than about 4.7%, less than about 4.6%, less than about 4.5%, less than about 4.4%, less than about 4.3%, less than about 4.2%, less than about 4.1%, or about 4.0% of the subject weight-adjusted dose.

In some embodiments, the average amount of solriamfetol that would be passed to an infant feeding from the breast milk produced by the subject treated with solriamfetol according to the methods disclosed herein is less than about 0.70 mg, about 0.69 mg, about 0.68 mg, about 0.67 mg, about 0.66 mg, about 0.65 mg, about 0.64 mg, about 0.63 mg, about 0.62 mg, about 0.61 mg, about 0.60 mg, or about 0.59 mg over 24 hours.

A daily dose of about 1 to about 2000 mg of solriamfetol or a pharmaceutically acceptable salt thereof may be administered to accomplish the therapeutic results disclosed herein. For example, a daily dosage of about 1-1000 mg, e.g., about 20-500 mg, in single or divided doses, is administered. In some embodiments, the daily dose may be about 0.01 to about 150 mg/kg body weight, e.g., about 0.2 to about 18 mg/kg body weight. In some embodiments, the dose contains about 1 mg to about 1000 mg of the drug or any range or value therein, e.g., about 10 mg to about 500 mg, e.g., about 37.5 mg, about 75 mg, about 150 mg, or about 300 mg. For example, in certain such embodiments, the total amount of drug may be selected from about 10, 20, 30, 40, 50, 60, 70, 80, 90, 100, 125, 150, 175, 200, 225, 250, 275, 300, or any range therein.

In one embodiment of the invention, solriamfetol is administered to the subject as needed to treat a disorder. The compound can be administered continuously or intermittently. In one embodiment, the compound is administered to the subject more than once a day, e.g., 2, 3, or 4 times per day, or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment the compound can be administered to build up to a certain level, then maintained at a constant level and then a tailing dosage.

In one aspect of the invention, solriamfetol is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, antipsychotics, anti-depressants, agents for neurological disorders, and chemotherapeutic agents. One therapeutic agent that can be administered during the same period is Xyrem®, sold commercially by Jazz Pharmaceuticals, which is used to treat narcolepsy and cataplexy. See U.S. Pat. Nos. 8,952, 062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults, and geriatric subjects. In some embodiments, the subject is postpartum, In some embodiments, the subject is a woman between the ages of 18 and 45 years.

Suitable subjects are generally lactating mammalian subjects. The term "mammal" as used herein includes, but is not limited to, humans, non-human primates, cattle, sheep, goats, pigs, horses, cats, dog, rabbits, rodents (e.g., rats or mice), etc. The human subject can be a lactating individual who is breastfeeding an infant frequently or on a regular basis. In some embodiments, the human subject is a woman. The woman may be between about 18 and 45 years of age. The term "breastfeeding" may also be referred to as chestfeeding, or grammatical variations thereof, refers to delivering breast milk of the individual directly to an infant, extracting breast milk from the individual using a device and subsequently delivering to an infant, extracting breast milk from the individual using a device and storing the breast milk for a period of time and subsequently delivering the stored breast milk to the infant, or a combination thereof.

The subject of the present disclosure can be in lactation, for example, an individual who is lactating (e.g., producing breast milk), nursing or breastfeeding. The subject can be in lactation after pregnancy, i.e., post-partum, or via induced lactation (e.g., with metoclopramide, oral contraceptives, herbal medications, stimulation via pumping, or any combination thereof.).

In some embodiments, the subject is between 1 day and 24 months postpartum, between about 1 day and 12 months postpartum, or between about 10 days and 12 months postpartum. In some embodiments, the subject expresses mature milk, which typically occurs about 10 to about 30 days (e.g., about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days) postpartum, or about 10 to about 20 days postpartum, or about 10 to about 20 days after beginning of milk expression in induced lactation. Infancy starts at birth and ends around the age of 2 years; accordingly, the infant stage being fed breast milk includes the breastfeeding period.

The subject can be a subject "in need of" the methods of the present invention, e.g., in need of the therapeutic effects of the inventive methods. For example, the subject can be a subject that is experiencing a disorder amenable to treatment with solriamfetol, is suspected of having a disorder amenable to treatment with solriamfetol, and/or is anticipated to experience a disorder amenable to treatment with solriamfetol, and the methods and compositions of the invention are used for therapeutic and/or prophylactic treatment.

Having described the present invention, the same will be explained in greater detail in the following examples, which are included herein for illustration purposes only, and which are not intended to be limiting to the invention.

EXAMPLES

Example 1. Phase 4 Clinical Trial in Breastfeeding Subjects

A Phase 4, open-label, single-dose study to evaluate the pharmacokinetics (PK) of solriamfetol in the breast milk and plasma of healthy postpartum women following oral administration of a 150 mg solriamfetol tablet.

The study was conducted in 6 healthy adult lactating women who were between 15 and 37 weeks postpartum and were administered a single oral dose of SUNOSI 150 mg. SUNOSI was excreted in breast milk with a milk to plasma AUC ratio of approximately 2:1. The median $T_{max}$ for SUNOSI in breast milk was approximately 1.1 hours, and the mean elimination half-life in breast milk was approximately 5.0 hours. The average amount that would be passed to the infant was estimated to be 0.59 mg over 24 hours, which is about 4.0% of the maternal dose on a weight-adjusted basis. The data from the lactation study indicate that SUNOSI is transferred to breastmilk in nursing mothers, with the relative infant dose (RID) is approximately 4% of the maternal weight-adjusted dosage. Data to assess the effects of SUNOSI on a breastfed infant or on milk production is not provided. The developmental and health benefits of breastfeeding should be considered along with the mother's clinical need for SUNOSI and any potential adverse effects on the breastfed child from SUNOSI or from the underlying maternal condition. Breastfed infants should be monitored for adverse reactions, such as agitation, insomnia, anorexia, and reduced weight gain.

Solriamfetol had a short systemic elimination half-life of 5.0 to 7.6 hours, and with once daily dosing the estimated accumulation ratio of 1.06 was marginally higher than 1, indicating essentially no accumulation with repeated dosing. Therefore, a single therapeutic dose of solriamfetol was administered in this study. Since the objective of this study was to evaluate solriamfetol PK in breast milk and plasma, as well as to estimate the daily drug dose received by the infant from breast milk, the highest approved therapeutic dose of 150 mg solriamfetol was administered.

The subjects were between 10 days and 52 weeks postpartum. The lower time limit of 10 days postpartum represented a time after which mature milk was developed (US FDA 2019). The upper time limit of 52 weeks postpartum was chosen based on a prospective study that showed that fat, total solids, and "energy" (kcal/dL) were all statistically increased in breast milk collected 12 to 18 months postpartum (N=25) compared with breast milk collected 1 to 12 months postpartum (N=35) (Czosnykowska Lukacka 2018). Also, there was a paucity of data regarding breast milk nutrient composition at >12 months postpartum (Wu 2018). The study included frequent maternal milk sample collections during a 72-hour period postdose to enable detection of the potential presence of solriamfetol in breast milk. Plasma concentrations of solriamfetol were also evaluated during the same time period to assess solriamfetol's potential accumulation in breast milk relative to the plasma.

Subjects were instructed to refrain from breastfeeding their infants for 72 hours postdose. Based on the drug's short half-life, this period (10× half-life) was expected to be of sufficient duration for complete elimination of solriamfetol from both the systemic circulation and breast milk.

Pharmacokinetic Results

All subjects in the PK Population were included in the PK analysis. Pharmacokinetic Population was defined as all subjects who received study drug and provided postdose breast milk or plasma PK data for at least one collection interval or time point. Subject 1003, 1004, and 1007 had multiple protocol deviations documented with regards to the timing of food consumption, however, these deviations are not likely to impact solriamfetol PK and these subjects were included in the descriptive statistics or PK parameter analysis. Furthermore, the PK of solriamfetol in fed versus fasted subjects satisfied the criteria for bioequivalence, indicating that solriamfetol can be taken regardless of food intake.

Figure 2:
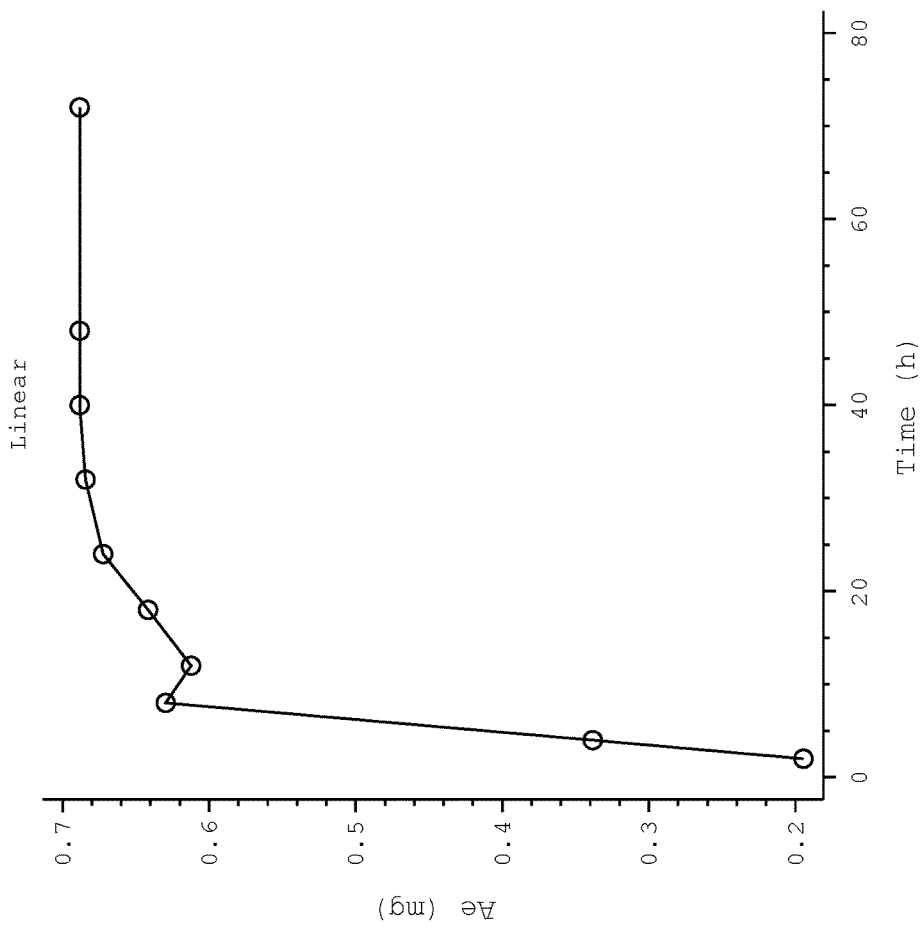
FIG. 2. Mean breast milk cumulative solriamfetol amount-time profiles on linear scale following a single-dose administration of solriamfetol 150 mg tablet.

The mean plasma and breast milk solriamfetol concentration time profiles are shown in FIG. 1. FIG. 1 shows the time course of mean plasma and breast milk solriamfetol concentrations on Day 1 following a single-dose administration of solriamfetol 150 mg tablet in the morning 2 hours after completion of a light breakfast. After reaching maximum solriamfetol concentrations approximately 1.00 to 3.00 hours after oral administration, plasma and breast milk exposures followed a parallel monoexponential decline. Solriamfetol concentrations in breast milk were approximately 2-fold higher than plasma concentrations The mean breast milk cumulative solriamfetol amount-time profiles are shown in FIG. 2. FIG. 2 shows the mean breast milk cumulative solriamfetol amount-time profiles following a single-dose administration of solriamfetol 150 mg tablet in the morning 2 hours after completion of a light breakfast. Arithmetic mean±SD amount excreted in breast milk over 72 hours was 0.6880±0.4672 mg. However, near complete excretion was observed within 24 hours of dosing.

No subjects had Rsq adjusted values <0.700, or % AUCex>20%, therefore Lambda_z and AUC0-inf related parameters were all considered reliable and included in descriptive statistics.

Table 1 summarizes the plasma and breast milk PK parameters for solriamfetol following single-dose administration.

Solriamfetol exposure was approximately 2-fold higher, on average, in breast milk than plasma with geometric mean $C_{max}$ of 1861 vs 892.5 ng/mL, $AUC_{0-t}$ of 12770 vs 6236 h*ng/ml, and $AUC_{0-inf}$ of 12940 vs 6340 h*ng/ml, respectively. The geometric mean milk:plasma ratio was 2.047.

Plasma solriamfetol $t_{max}$ (from 0.98 to 3.02 hours, median 1.25 hours) was similar to breast milk (from 1.00 to 3.00 hours, median 1.12 hours).

The geometric mean solriamfetol $t_{1/2}$ appear similar between plasma (4.751 hours) and breast milk (4.869 hours). Furthermore, the geometric mean plasma solriamfetol CL/F was 23.66 L/h and $V_z/F$ was 162.2 L. Geometric mean $A_{milk}$ was 0.5651 mg, with a daily and relative infant dose of 0.5856 mg and 4.030%, respectively.

TABLE 1

Summary of Pharmacokinetic Parameters for Solriamfetol in Plasma and Breast Milk (Pharmacokinetic Population)

| Pharmacokinetic Parameters | Arithmetic Mean (CV %) [Geometric Mean] | |
|---|---|---|
| | Plasma (N = 6) | Breast Milk (N = 6) |
| $AUC_{0-inf}$ (h * ng/ml) | 6543 (27.7) [6340] | 13850 (41.0) [12940] |
| $AUC_{0-t}$ (h * ng/ml) | 6439 (27.9) [6236] | 13700 (41.4) [12770] |
| $C_{max}$ (ng/mL) | 905.2 (18.0) [892.5] | 2068 (48.7) [1861] |
| $t_{max}$ (h)$^a$ | 1.25 (0.98, 3.02) | 1.12 (1.00, 3.00) |
| Lambda_z (1/h) | 0.1478 (19.1) [0.1459] | 0.1446 (18.8) [1424] |
| $t_{1/2}$ (h) | 4.804 (15.2) [4.751] | 4.954 (21.4) [4.869] |
| CL/F (L/h) | 24.40 (26.8) [23.66] | NC |
| $V_z/F$ (L) | 168.9 (31.9) [162.2] | NC |
| Milk:Plasma Ratio | NC | 2.136 (35.8) [2.047] |
| $A_{milk}$ (mg) | NC | 0.6880 (67.9) [0.5651] |
| Daily Infant Dose (mg) | NC | 0.6927 (63.5) [0.5856] |
| Relative Infant Dose (%) | NC | 4.602 (60.6) [4.030] |

NC = not calculated.
Note:
CV % was based on the arithmetic mean.
$^a$Median (min, max).

Pharmacokinetic Conclusion

Solriamfetol $t_{max}$ for both plasma and breast milk were similar and ranged between 1 to 3 hours. After reaching maximum solriamfetol concentrations, plasma and breast milk exposures followed a parallel monoexponential decline. Solriamfetol breast milk exposure ($C_{max}$ and AUCs) was 2-fold higher than plasma. Furthermore, the geometric mean milk:plasma ratio was 2.047. The solriamfetol $t_{1/2}$ appeared similar in plasma and breast milk at approximately 5 hours. This study was exclusively in post-partum women, a very different population than the ones for the studies reported in the Pharmacokinetics section of the current Sunosi® label which were healthy male and female patients who were not postpartum. The Sunosi® label reports oral bioavailability of solriamfetol is approximately 95% with peak plasma concentration of solriamfetol occurs at a median $T_{max}$ of 2 hours (range 1.25 to 3.0 hours) post-dose under fasted conditions healthy male and female patients who were not postpartum. Indeed, while the median $T_{max}$ reported for healthy male and female patients who were not postpartum is reported in the label as 2 hours, the $T_{max}$ in the present lactation study is 1 hour. Similarly, the apparent mean elimination plasma half-life is 7.1 hours for healthy male and female patients who were not postpartum on the Sunosi® label compared to 4.8 hours in plasma and 4.95 hours in breast milk in the present lactation study.

CL/F and were determined for plasma solriamfetol only. Arithmetic mean of CL/F was 24.40 L/h and was 168.9 L. $A_{milk}$, daily infant dose, and relative infant dose were determined for breast milk solriamfetol only. Arithmetic mean of was 0.6880 mg, daily infant dose was 0.6927 mg, and relative infant dose was 4.602% Safety Results Adverse Events: The overall summary of Treatment Emergent Adverse Events (TEAEs) is summarized in Table 2. A total of 3 (50%) subjects had at least 1 AE; of 2 (33.3%) subjects had TEAEs related to the study drug and 1 (16.7%) subject had TEAE unrelated to the study drug. The mild TEAEs were reported in 2 (33.3%) subjects and moderate TEAEs were reported in 1 (16.7%) subject. No SAEs were reported in the study. None of the subjects discontinued due to TEAEs.

TABLE 2

Overall Summary of Treatment Emergent Adverse Events (Safety Population)

| Category | Solriamfetol 150 mg (N = 6) n (%) |
| --- | --- |
| Subjects with at least 1 AE | 3 (50.0) |
| Subjects with an | |
| AE considered related to study drug | 2 (33.3) |
| AE considered unrelated to study drug | 1 (16.7) |
| Subjects with<sup>a</sup> | |
| SAE | 0 |
| SAE considered related to study drug | 0 |
| SAE considered unrelated to study drug | 0 |
| Subjects who discontinued due to | |
| AE | 0 |
| AE considered related to study drug | 0 |
| AE considered unrelated to study drug | 0 |
| Subjects with<sup>a</sup> | |
| Mild AE | 2 (33.3) |
| Moderate AE | 1 (16.7) |
| Severe AE | 0 |
| Life-threatening AE | 0 |
| Fatal AE | 0 |

AE = adverse event;
N = number of subjects exposed;
SAE = serious adverse event.
Note:
Percentages are based on N
<sup>a</sup>Subjects reporting an adverse event in more than one category were counted only once for the category.

Out of 3 subjects reporting TEAEs, 1 subject had dizziness and headache (SOC: Nervous system disorder), 1 subject had agitation (SOC: Psychiatric disorder), and 1 subject had an event of headache (SOC: Nervous system disorder) (Table 3). A total of 4 TEAEs were reported where 3 TEAEs (dizziness, headache, and agitation) were mild and 1 TEAE (headache) was moderate in intensity. All the 3 mild TEAEs were related to the study drug and the moderate TEAE was unrelated to the study drug. All the TEAEs were resolved.

TABLE 3

Summary of Treatment Emergent Adverse Events by System Organ Class, Preferred Term (Safety Population)

| System Organ Class (SOC) Preferred Term (PT) | Solriamfetol 150 mg (N = 6) n (%) |
| --- | --- |
| Nervous system disorders | 2 (33.3) |
| Dizziness | 1 (16.7) |
| Headache | 2 (33.3) |
| Psychiatric disorders | 1 (16.7) |
| Agitation | 1 (16.7) |

N = number of subjects exposed.
Notes:
Percentages are based on N.
A subject with multiple adverse events within a primary system organ class was counted only once.
A subject with multiple occurrences of an AE was counted only once in the AE category
System organ classes are presented in alphabetical order; preferred terms are presented within system organ class in alphabetical order
Adverse events were coded using the MedDRA coding dictionary, MedDRA180 Mixed Vital Signs: There were no major changes in vital sign parameters from baseline to Day 1 2 hours and 4 hours, Day 2, Day 3, and Day 4. The summary of clinically notable vital signs at any post-baseline visit are summarized in Table 4.

TABLE 4

Summary of Clinically Notable Vital Signs at Any Post-baseline Visit/Timepoint (Safety Population)

| Parameter (Unit) | Criteria | Solriamfetol 150 mg (N = 6) n (%) |
| --- | --- | --- |
| Systolic blood pressure (mmHg) | Blood pressure change by >20% from the study baseline value/recordings | 1 (16.7) |
| Diastolic blood pressure (mmHg) | Average diastolic blood pressure ≥95 mmHg or ≤60 mmHg | 2 (33.3) |
| Pulse rate (beats/min) | Pulse change by >20% from the study baseline value/recordings | 2 (33.3) |
| Body temperature (C.) | Change in body temperature >1.8% from the subjects baseline temperature recordings | 1 (16.7) |

N = number of subjects exposed.
Notes:
Percentages are based on N.
Baseline was defined as the last non-missing measurement taken prior to dosing. All post-baseline assessments, including unscheduled, were considered for this summary.

There were no major changes in ECG parameters from baseline to Day 1 predose and 2 hours, Day 2, Day 3, and Day 4. No abnormal clinically significant ECG findings were reported.

The summary of clinically notable ECG findings at any post-baseline visit are summarized in Table 5.

TABLE 5

Summary of Clinically Notable Electrocardiograms at Any Post-baseline Visit/Timepoint (Safety Population)

| Parameter (Unit) | Criteria | Solriamfetol 150 mg (N = 6) n (%) |
|---|---|---|
| ECG mean heart rate (bpm) | Ventricular rate ≥100 beats/min or ≤60 beats/min | 2 (33.3) |
| PR interval, single beat (msec) | PR interval ≥200 msec or ≤120 msec | 2 (33.3) |
| QRS duration, single beat (msec) | QRS duration ≥100 msec or ≤80 msec | 4 (66.7) |
| QT interval, single beat (msec) | QT interval ≥440 msec or ≤350 msec | 1 (16.7) |

N = number of subjects exposed.
Notes:
Percentages are based on N.
Baseline was defined as the last non-missing measurement taken prior to dosing. All post-baseline assessments, including unscheduled, were considered for this summary.

None of the subjects had reported any suicidal ideation or event under Columbia-Classification Algorithm for Suicide Assessment.

Safety Conclusions

Overall, 6 subjects were enrolled in the safety analysis and treated with the single oral dose of Solriamfetol which was safe and well tolerated.

Out of 6 subject 3 (50%) subjects had at least 1 AE. Out of 3 subjects reporting TEAEs: 1 subject had dizziness and headache (SOC: Nervous system disorder) both of mild intensity and were related to study drug; 1 subject had agitation (SOC: Psychiatric disorder) of mild intensity and was related to study drug; 1 subject had an event of headache (SOC: Nervous system disorder) of moderate intensity and was not related to study drug. No SAEs, deaths, or other significant AEs were reported in the study. None of the subjects discontinued due to TEAEs. None of the subjects had abnormal, clinically significant laboratory findings. There were no major changes in vital sign from baseline to Day 1 2 hours and 4 hours, Day 2, Day 3, and Day 4 and ECG parameters from baseline to Day 1 predose and 2 hours, Day 2, Day 3, and Day 4. None of the subjects had reported any suicidal ideation or event under Columbia-Classification Algorithm for Suicide Assessment.

DISCUSSION

The instant study was a Phase 4, open-label, single-dose study to evaluate the PK of solriamfetol in the breast milk and plasma of healthy postpartum women following oral administration of a 150 mg solriamfetol tablet. A total of 6 subjects were enrolled and were included in both PK and safety analysis. All the 6 subjects had completed the study. There were no premature discontinuations reported in the study.

The primary objective (PK) of this study was to assess the PK of solriamfetol in plasma and breast milk after single oral dose of solriamfetol 150 mg tablet in the morning 2 hours after completion of a light breakfast. Solriamfetol exposure was approximately 2-fold higher, on average, in breast milk than plasma with geometric mean $C_{max}$ of 1861 vs 892.5 ng/ml, $AUC_{0-t}$ of 12770 vs 6236 h*ng/ml, and $AUC_{0-inf}$ of 12940 vs 6340 h*ng/ml, respectively. The geometric mean milk:plasma ratio was 2.047. Plasma solriamfetol $t_{max}$ (from 0.98 to 3.02 h, median 1.25 h) was similar to breast milk (from 1.00 to 3.00 hours, median 1.12 hours). The geometric mean solriamfetol $t_{1/2}$ appeared similar between plasma (4.751 hours) and breast milk (4.869 hours). Furthermore, the geometric mean plasma solriamfetol CL/F was 23.66 L/h and $V_z/F$ was 162.2 L. Geometric mean $A_{milk}$ was 0.5651 mg, with a daily and relative infant dose of 0.5856 mg and 4.030%, respectively.

The secondary objective of study was to assess the safety and tolerability of the solriamfetol in healthy postpartum women. Overall, the study drug was safe and well tolerated. No SAEs, deaths, or other significant AEs were reported in the study. None of the subjects discontinued due to TEAEs. Out of 6 subjects, 3 subjects reported adverse events. All AE (dizziness, headache, and agitation) were of mild intensity except 1 AE (headache) was of moderate intensity.

None of the subjects had abnormal or clinically significant laboratory findings. There were no major changes in vital sign from baseline to Day 1 2 hours and 4 hours, Day 2, Day 3, and Day 4 and ECG parameters from baseline to Day 1 predose and 2 hours, Day 2, Day 3, and Day 4. None of the subjects had reported any suicidal ideation or event under Columbia-Classification Algorithm for Suicide Assessment.

CONCLUSION

Solriamfetol $T_{max}$ for both plasma and breast milk were similar and ranged between 1 to 3 hours. After reaching maximum solriamfetol concentrations, plasma and breast milk exposures followed a parallel monoexponential decline. Solriamfetol breast milk exposure ($C_{max}$, AUCs) was 2-fold higher than plasma. Furthermore, the geometric mean milk:plasma ratio was 2.047. Solriamfetol $t_{1/2}$ appeared similar in plasma and breast milk at approximately 5 hours. Solriamfetol was safe and well tolerated.

METHODOLOGY

On Day −1, eligible subjects underwent the baseline procedures. On Day 1, 2 hours after a light breakfast, subjects were to receive a single dose of solriamfetol 150 mg with 240 mL of water. Subjects had to fast for approximately 4 hours after the first dose; water was allowed except for 1 hour before and 1 hour after dosing with the study drug.

Pharmacokinetic analysis of breast milk obtained from both breasts (by pumping) was evaluated prior to dose administration and at intervals up to 72 hours postdose. Blood samples were also collected for plasma solriamfetol quantitation and PK analysis predose and at timepoints up to 72 hours postdose. Solriamfetol breast milk and plasma concentrations were measured using validated bioanalytical methods. Safety was assessed throughout the study by 12-lead ECG, vital sign measurements, the Columbia-Suicide Severity Rating Scale (C-SSRS), and the incidence of adverse events (AE).

The study drug was yellow, film-coated tablets that contained the excipients hydroxypropyl cellulose and magnesium stearate and a polymer film coat (Opadry®).

The total overall study duration (first subject screened to safety follow-up of last subject) was approximately 11 months.

Vital signs (blood pressure, pulse rate, temperature, and respiratory rate) were measured with the subject in a seated or supine position and resting for at least 5 minutes prior to taking the measurement. The dominant arm was used for blood pressure and pulse rate measurements. On Day 1, vital signs were collected at predose, and at approximately 2 (blood pressure and pulse) and 4 hours (blood pressure and pulse) postdose.

12-lead ECG was taken with the subject in a supine position and resting for at least 10 minutes prior to taking the measurement. On Day 1, ECGs were collected predose and at approximately 2 hours postdose.

Subjects must fast for at least 8 hours before chemistry and hematology blood draws. All clinical laboratory tests were performed at Screening only (rescreening is permitted).

Screening/Baseline C-SSRS version at Screening, and since Last Visit version on Day −1 and Day 2 (or at ET).

Breast milk collection occurred at −2 to 0 (prior to dose), 0-2, 2-4, 4-8, 8-12, 12-18, 24-32, 32-40, 40-48 and 48-72 hours postdose on Days 1-4.

Blood samples for plasma PK evaluation were collected at the following time points: Predose, 1, 1.5, 3, 6, 8.5, 10, 13, 15, 21, 24, 28, 36, 44, and 72 hours following dosing on Day 1. General study methodology is outlined in Table 6.

TABLE 6

| Screening | Check-in (Baseline) | Study drug dosing | Check-out | Safety Follow-up | Lactation Follow-up |
|---|---|---|---|---|---|
| | | ---------PK sampling--------- | | | |
| Days −21 to −2 | Day −1 | Day 1 | Day 4 | Days 9-11 | Days 39-41 |

Standardized meals include meals as needed on Day −1, a light breakfast approximately 2.5 hours before dosing on Day 1 (to be completed approximately 2 hours before dosing) followed by lunch approximately 4 hours after dosing, dinner approximately 8 hours after dosing, and a snack approximately 11 hours after dosing, and standardized meals thereafter.

Record was from 30 days prior to screening through the Safety Follow Up telephone call 5 to 7 days after check-out from the study facility (at Day 4 or ET).

Adverse events were monitored throughout the study by safety assessments, observations, and subject reporting, including the Safety FU telephone call 5-7 days (i.e., Days 9-11) after check-out from the study facility on Day 4, or ET.

Breast milk collection: Solriamfetol concentration in breast milk and plasma was evaluated based on samples collected prior to and postdose on Days 1 to 4. Breast milk was collected from both breasts, using electronic breast pumps, during the following intervals: From −2 to 0 at predose and at 0 to 2, 2 to 4, 4 to 8, 8 to 12, 12 to 18, 18 to 24, 24 to 32, 32 to 40, 40 to 48, and 48 to 72 hours postdose on Day 1. The midpoint of each breast milk collection interval was used as the time variable.

Breast milk was collected as often as needed during the assigned intervals; however, at the end of each interval, breast milk was pumped from both breasts and collected. At the end of each collection interval, all milk expressed from both breasts during that interval was pooled. The milk was thoroughly mixed by gently inverting the collection vessel 10 times to ensure homogeneity in milk composition. The weight and volume of the collected milk during each interval was also recorded.

Serial blood samples (4 mL) were collected and dispensed into labeled K2EDTA tubes. The actual time of blood collection for all samples was recorded on the eCRF. Solriamfetol concentration in breast milk and plasma were determined using a validated bioanalytical method (LC-MS/MS) at Origin Bioanalytical Laboratory. The analytical range (lower limit of quantitation [LLOQ] to upper limit of quantitation) for plasma solriamfetol was 8.42 to 4210.00 ng/mL, and breast milk solriamfetol was 10.0 to 8000 ng/mL.

Pharmacokinetic parameters were derived with Phoenix® WinNonlin® Version 8.3 (Certara, Inc., Princeton, New Jersey, USA) and/or SAS® Version 9.4 (SAS Institute, Inc., Cary, North Carolina, USA).

Criteria for Subjects: Each subject who met the following criteria were enrolled in the study: Healthy adult female 18 to 50 years of age, inclusive, at the time of consent; At least 50 kg body weight and body mass index (BMI) within 18 to 35 kg/m² inclusive; Postpartum between 10 days and 52 weeks, inclusive, after delivery of a normal, healthy infant by the time of dosing, and actively lactating from both breasts; If breastfeeding, agreed to withhold breastfeeding their infant(s) from approximately 2 hours before dosing to approximately 72-hours after dosing and resumed breastfeeding after completion of study Day 4 procedures or would have made a decision to wean their infants before enrollment in the study; Agreed not to use nicotine-containing products including tobacco (cigarettes, cigars, chewing tobacco, snuff), e-cigarettes, and nicotine lozenge/gum/patch within 3 days prior to check-in on Day −1, and for the duration of the study; Had used a medically acceptable method of contraception for at least the 2 months prior to dosing on Day 1, and consented to use a medically acceptable method of contraception throughout the entire study period and for 30 days after the study was completed; Agreed to comply with study-specified diet while in the study; Able to understand and comply with study requirements; Ensured that their breastfed infant(s) was able to feed from a bottle before study participation begins; Agreed to ensure nutrition was available for their infant(s) through stored breast milk, or alternative nutritional sources as necessary, for the duration of the study; Participants who: Were fully vaccinated for at least 14 days after the last (or only) dose of the severe acute respiratory syndrome coronavirus 2 (SARS-CoV-2 [COVID-19]) vaccine; or Elected not to be vaccinated prior to the study, with Participant who chooses not to be fully vaccinated prior to the start of the study did not receive any dose of the COVID-19 vaccine and remained on the study.

Clinical laboratory tests including hematology, serum chemistry, urinalysis. and thyroid panel, were collected at Screening only.

A complete physical examination included, at a minimum, assessment of the cardiovascular, respiratory, gastrointestinal, and neurological systems. Height and weight were also measured and recorded. At Screening and Baseline/Randomization visits, BMI was calculated by the site in order to verify eligibility.

Vital signs included oral temperature, pulse rate, respiratory rate, and BP. Clinically significant abnormal vital signs results reported during Screening/Randomization were recorded as medical history and those reported after study drug were recorded as AEs.

Blood pressure and pulse measurements were assessed with the subject in a seated or supine position and resting for at least 5 minutes prior to taking the measurement. The dominant arm was used for blood pressure and pulse rate measurements. On Day 1, vital signs were collected at predose, and at approximately 2 (blood pressure and pulse) and 4 hours (blood pressure and pulse) postdose.

The 12-lead ECGs were collected at Screening, Day −1 until Day 4. Single 12-lead ECG was obtained using an ECG machine that automatically calculated the heart rate and measured PR, QRS, QT, and corrected QT interval (QTc)

intervals. Any abnormal safety assessments including ECG readings considered clinically significant in the medical and scientific judgment of the investigator were reported as an AE. The investigator had to review the ECG and document it in the source documents. Clinically significant abnormal ECG results reported during Screening were recorded as medical history and those reported after study drug were recorded as AEs.

All laboratory tests were to be performed in accordance with Laboratory Manual. The tests detailed in Table 7 were performed by the central laboratory. Additional tests might be performed at any time during the study as determined necessary by the investigator or required by local regulations.

All laboratory tests with abnormal values considered clinically significant during the study or within 14 days after the last dose of study drug (and considered by the investigator to be related to study drug) were repeated until the values return to normal or Baseline or were no longer considered clinically significant by the investigator or medical monitor. If clinically significant values did not return to normal/Baseline within a period of time judged reasonable by the investigator, the etiology were to be identified.

TABLE 7

Safety Laboratory Test

| Hematology: | Serum Chemistry: |
|---|---|
| Complete blood count (CBC), including platelet count and white blood cell count (WBC) with differential (absolute count and percent) | Albumin (ALB) |
| | Alkaline phosphatase (ALK-P) |
| | Alanine aminotransferase (ALT) |
| | Aspartate aminotransferase (AST) |
| Urinalysis: | Blood urea nitrogen (BUN) |
| Appearance | Calcium (Ca) |
| Bilirubin | Carbon dioxide (CO2) |
| Color | Chloride (Cl) |
| Glucose | Creatinine |
| Ketones | Creatine kinase |
| Nitrite | Glucose |
| Occult blood | Phosphorus |
| pH | Potassium (K) |
| Protein | Sodium (Na) |
| Specific gravity | Total bilirubin |
| Urobilinogen | Direct bilirubin |
| Leukocyte esterase | Total cholesterol |
| | Total protein |
| | Triglycerides |
| | Uric acid |
| Drug Screening: | Pregnancy*: |
| Urine Drug Screen (amphetamines, barbiturates, benzodiazepines, cocaine, marijuana, opiates, phencyclidine) | Serum at Screening |
| | Urine at Baseline (Day -1) |
| Breath alcohol test | |

ALB = albumin;
ALK-P = alkaline phosphatase;
ALT = alanine aminotransferase;
AST = aspartate aminotransferase;
BUN = blood urea nitrogen;
Ca = calcium;
CBC = complete blood count;
CO2—carbon dioxide;
Cl = chlorine;
K = potassium;
Na = sodium;
WBC = white blood cell count.
*Pregnancy screening required for all subjects in the study.

Statistical/Analytical

Unless otherwise specified, continuous data was summarized using descriptive statistics comprising of the number of subjects exposed (N) and with data to be summarized (n), mean, standard deviation (SD), median, minimum (min), maximum (max), geometric mean (Geo-mean), coefficient of variation (CV %), and geometric coefficient of variation (CV %). Categorical variables were presented using counts and percentages. Analyses and summary outputs were generated using SAS® Version 9.4 (SAS Institute, Inc., Cary, North Carolina, USA).

The PK Population consisted of all subjects who received study drug and provided postdose breast milk or plasma PK data for at least one collection interval or time point. This population was used for evaluable PK concentration data and PK parameter summaries and listings. The Safety Population consisted of all subjects who received the dose of study drug. This population was used for demographic and baseline characteristics and for safety data summaries and listings.

Pharmacokinetic concentrations and parameters were summarized using descriptive statistics, including n, arithmetic mean, SD, coefficient of variation (CV %), median, min, max, Geometric mean (Geo-mean) and the geometric coefficient of variation (Geo-CV %). For the PK parameter $t_{max}$, only n, median, minimum, and maximum was presented.

Subjects with partial data were evaluated on a case-by-case basis to determine if sufficient data was available for reliable calculation of PK parameters. In case of an incomplete milk collection (partial/spilt sample with inaccurate information of the total milk volume of the by-interval samples), the by-interval recovery was listed but not included in the summary, and cumulative recovery was only reported through the most recent prior complete milk collection. By-interval data during which a subject was unable to lactate (produce any milk), was treated as an amount of zero (for the affected interval) in the summation of cumulative recovery calculation.

Plasma and milk concentrations were summarized using descriptive statistics. Concentrations that were below the lower limit of quantitation (BLQ) were treated as follows for the computation of descriptive statistics:

The summary statistics at a time with one or more BLQ values were calculated by assigning ½ LLOQ to all values less than LLOQ. If the calculated arithmetic (and geometric) mean value was BLQ, then SD and CV % were presented as "ND.", and the mean was presented as "BLQ. However, since a high proportion of BLQ values may have affected the SD; if more than 50% of values were imputed, then no mean was calculated for that time point and again a value of BLQ was presented only for the mean value. Within the summary statistics, any minimum, or median values that were calculated to be BLQ were presented as BLQ within the summary presentation.

Concentrations collected outside of the protocol allowed sampling windows were included in descriptive statistics, unless the PK scientist observed that the deviation was substantial enough to impact descriptive statistics. In this case, the excluded concentrations were identified in the CSR.

For plotting arithmetic mean concentration profiles: The arithmetic mean value at a time with one or more BLQ values were calculated by assigning ½ LLOQ to all values BLQ. If the calculated mean value was BLQ, then that time point was plotted as zero in the mean pharmacokinetic profiles. However, since a high proportion of BLQ values may have affected the SD; if more than 50% of values were imputed, then no mean was calculated for that time point and again a value of zero plotted. A line with a label of LLOQ in the concentration axis was overlaid to show the level of LLOQ.

Safety analyses were based on the Safety Population. The secondary endpoints for evaluating subject safety and tolerance were the incidence of reported AEs and the laboratory test results for all subjects.

Adverse events: Adverse events recorded in the electronic case report forms (eCRFs) were coded to SOC and PT using the Medical Dictionary for Regulatory Activities (MedDRA). Treatment-emergent adverse events (TEAEs) are defined as any event with onset date on or after the first dose of study drug or any ongoing event that worsened in severity after the date of the first dose of study drug or any event that was present at baseline but was subsequently considered drug-related by the investigator through the end of the study. The incidence of TEAEs were presented by severity, relationship to study drug, start and end date, seriousness, and outcome. The investigator assessed the severity and relatedness of each AE to study drug. Columbia-Suicide Severity Rating Scale (C-SSRS) data were summarized at scheduled visits and were listed. Other safety analyses were performed as appropriate.

12 Lead ECG: The number and percentage of subjects who had the following postbaseline clinically notable ECG interval abnormality was summarized: Ventricular rate≥100 beats/min or ≤60 beats/min; PR interval≥200 msec or ≤120 msec; QRS duration≥100 msec or ≤80 msec; QT interval≥440 msec or ≤350 msec; QTc Bazett and QTc Fredericia≥470 msec or ≤330 msec; RR interval≥1200 msec or ≤600 msec; and QTc Bazette and QTc Fredericia increase from study Baseline Value>30 msec.

Vital Signs: The following clinically notable vital sign abnormalities were presented: Average systolic blood pressure≥150 mmHg or ≤80 mmHg; Average diastolic blood pressure≥95 mmHg or ≤60 mmHg; Average heart rate≥120 bpm or ≤50 bpm; Respiratory rate<10 breaths/min or >24 breaths/min; Body temperature>37.9° C. or <35.5° C.; Systolic and diastolic blood pressure change by >20% from the study baseline value/recordings; Pulse change by >20% from the study baseline value/recordings; Change in body weight by ≥7% from subject's baseline value (weight loss/weight gain); and Change in body temperature>1.8% from the subject's baseline temperature recordings.

Physical Examination: Physical examination data for each subject was presented in a listing. A clinically significant adverse change (i.e., worsening) of a physical examination finding after screening was recorded as an AE.

Disposition of Subjects. A total of 6 subjects were enrolled and treated in the study. All 6 subjects had completed the study. There were no premature discontinuations reported in the study. All 6 subjects received the study drug (safety population) and provided post-dose breast milk or plasma PK data for at least one collection interval or time point (PK population). All 6 subjects were females and belonged to not Hispanic or Latino ethnicity. The mean (SD) of age, weight, height, and BMI of the overall population was 28.7 (5.54) years, 79.15 (12.162) kg, 168.62 (6.013) cm, and 27.90 (4.513) kg/m², respectively.

TABLE 8

Demographics and Baseline Characteristics (Safety Population)

| Characteristic | Solriamfetol 150 mg (N = 6) |
|---|---|
| Age (years) | |
| n | 6 |
| Mean (SD) | 28.7 (5.54) |
| Median | 29.5 |
| Min, Max | 21, 35 |
| Gender, n (%) | |
| Female | 6 (100%) |
| Missing | 0 |
| Race, n (%) | |
| White | 3 (50.0) |
| Black or African American | 3 (50.0) |
| Missing | 0 |
| Ethnicity, n (%) | |
| Not Hispanic or Latino | 6 (100%) |
| Missing | 0 |
| n | 6 |
| Mean (SD) | 168.62 (6.013) |
| Median | 170.00 |
| Min, Max | 160.0, 177.5 |
| Weight (kg) | |
| n | 6 |
| Mean (SD) | 79.15 (12.162) |
| Median | 77.90 |
| Min, Max | 64.1, 99.1 |
| BMI (kg/m²) | |
| n | 6 |
| Mean (SD) | 27.90 (4.513) |
| Median | 27.95 |
| Min, Max | 22.4, 34.3 |

BMI = body mass index;
N = number of subjects exposed
Note:
Percentages are based on N.

Prior and Concomitant Medication: Two subjects had taken medications during the study for AEs. One subject received acetaminophen and other received ibuprofen.

Medical and Surgical History: A total of 5 of 6 subjects had the medical and surgical history. Of these subjects, 1 subject had the medical history of appendectomy, C-section, and tubal ligation. One subject had asthma and C-section. One subject had cholelithiasis, pancreatitis, and gall bladder removal. One subject had umbilical hernia repair, heartburn, and C-section, and 1 subject had natural childbirth and hip pain dur to natural childbirth.

REFERENCES

Czosnykowska-Łukacka, M., Królak-Olejnik, B., & Orczyk-Pawiłowicz, M. (2018). Breast Milk Macronutrient Components in Prolonged Lactation. Nutrients, 10(12), 1893. Doi: 10.3390/nu10121893.

Jones B. E. (2000). Basic mechanisms of sleep-wake states. In: Kryger, M. H.; Roth, T.; and Dement, W. C., eds. Principles and Practice of Sleep Medicine 3d ed. Philadelphia: W. B Saunders. pp. 134-154.

Li Y., Panossian, L. A., Zhang, J., Zhu, Y., Zhan, G., Chou, Y. T., Fenik, P., Bhatnagar, S., Piel, D. A., Beck, S. G., & Veasey, S. (2014). Effects of chronic sleep fragmentation on wake-active neurons and the hypercapnic arousal response. Sleep, 37(1), 51-64. Doi: 10.5665/sleep.3306.

Lockwood P. A., Pauer, L., Scavone, J. M., Allard, M., Mendes da Costa, L., Alebic-Kolbah, T., Plotka, A., Alvey, C. W., & Chew, M. L. (2016). The Pharmacokinetics of Pregabalin in Breast Milk, Plasma, and Urine of Healthy Postpartum Women. Journal of human lactation: official journal of International Lactation Consultant Association, 32(3), NP1-NP8. Doi: 10.1177/0890334415626148.

Posner K., Brown, G. K., Stanley, B., Brent, D. A., Yershova, K. V., Oquendo, M. A., Currier, G. W., Melvin, G. A., Greenhill, L., Shen, S., & Mann, J. J. (2011). The Columbia-Suicide Severity Rating Scale: initial validity and internal consistency findings from three multisite studies with adolescents and adults. The American journal of psychiatry, 168(12), 1266-1277. Doi:10.1176/appi.ajp.2011.10111704.

Siegel J. M. Brainstem mechanisms generating REM sleep. In: Principals and Practice of Sleep Medicine, Second Edition. Edited by M. K. Kryger, T. Roth, W. C. Dement. New York: Saunders, 2000.

Tsujino N., Tsunematsu, T., Uchigashima, M., Konno, K., Yamanaka, A., Kobayashi, K., Watanabe, M., Koyama, Y., & Sakurai, T. (2013). Chronic alterations in monoaminergic cells in the locus coeruleus in orexin neuron-ablated narcoleptic mice. PloS one, 8(7), e70012. Doi:10.1371/journal.pone.0070012.

US Food and Drug Administration. Center for Drug Evaluation and Research (2019). Guidance for Industry. Clinical Lactation Studies: Considerations for Study Design. Draft guidance. Center for Drug Evaluation and Research, US Food and Drug Administration, Rockville, MD.

US Food and Drug Administration. Center for Drug Evaluation and Research. May 2019. Guidance for Industry. Clinical Lactation Studies: Considerations for Study Design. Draft guidance. Center for Drug Evaluation and Research, US Food and Drug Administration, Rockville, MD.

Wisor J. P., Nishino, S., Sora, I., Uhl, G. H., Mignot, E., & Edgar, D. M. (2001). Dopaminergic role in stimulant-induced wakefulness. The Journal of neuroscience: the official journal of the Society for Neuroscience, 21(5), 1787-1794. Doi: 10.1523/JNEUROSCI.21-05-01787.2001.

Wu X., Jackson, R. T., Khan, S. A., Ahuja, J., & Pehrsson, P. R. (2018). Human Milk Nutrient Composition in the United States: Current Knowledge, Challenges, and Research Needs. Current developments in nutrition, 2(7), nzy025. Doi: 10.1093/cdn/nzy025.

Zhu Y., Fenik, P., Zhan, G., Xin, R., & Veasey, S. C. (2015). Degeneration in Arousal Neurons in Chronic Sleep Disruption Modeling Sleep Apnea. Frontiers in neurology, 6, 109. Doi:10.3389/fneur.2015.00109.

The foregoing is illustrative of the present invention and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method of reducing the risk of insomnia in an infant fed breast milk obtained from a subject treated with solriamfetol, wherein the method provides a daily infant dose of solriamfetol of about 0.3 mg or lower, the method comprising:

orally administering the solriamfetol to the subject at a daily dose of about 150 mg; and feeding the infant breast milk obtained from the subject at least about 5 hours after administering the solriamfetol to the subject;

thereby decreasing the potential for insomnia from solriamfetol in the infant.

2. The method of claim 1, wherein the infant does not experience insomnia due to solriamfetol dose.

3. The method of claim 1, wherein the subject is from 1 day to 24 months postpartum.

4. The method of claim 1, wherein the subject is from 10 days to 12 months postpartum.

5. The method of claim 1, wherein the subject is being treated with solriamfetol for excessive daytime sleepiness, narcolepsy, obstructive sleep apnea, shift work disorder, attention deficit hyperactivity disorder, depression, binge eating disorder, Parkinson's disease, or cognitive impairment.

6. The method of claim 5, wherein the excessive daytime sleepiness is associated with narcolepsy, obstructive sleep apnea, shift work, major depression, or Parkinson's disease.

7. The method of claim 5, wherein the cognitive impairment is associated with narcolepsy, obstructive sleep apnea, shift work, Parkinson's disease, or attention deficit hyperactivity disorder.

8. The method of claim 1, wherein the subject is being treated with solriamfetol to improve wakefulness.

9. The method of claim 1, wherein the subject is a woman between the ages of 18 and 50 years.

10. A method of reducing the risk of insomnia in an infant fed breast milk obtained from a subject treated with solriamfetol, wherein the method provides a daily infant dose of solriamfetol of about 0.15 mg or lower, the method comprising:

orally administering the solriamfetol to the subject at a daily dose of about 75 mg; and feeding the infant breast milk obtained from the subject at least about 5 hours after administering the solriamfetol to the subject;

thereby decreasing the potential for insomnia from solriamfetol in the infant.

11. The method of claim 10, wherein the infant does not experience insomnia due to solriamfetol dose.

12. The method of claim 10, wherein the subject is from 1 day to 24 months postpartum.

13. The method of claim 10, wherein the subject is from 10 days to 12 months postpartum.

14. The method of claim 10, wherein the subject is being treated with solriamfetol for excessive daytime sleepiness, narcolepsy, obstructive sleep apnea, shift work disorder, attention deficit hyperactivity disorder, depression, binge eating disorder, Parkinson's disease, or cognitive impairment.

15. The method of claim 14, wherein the excessive daytime sleepiness is associated with narcolepsy, obstructive sleep apnea, shift work, major depression, or Parkinson's disease.

16. The method of claim 14, wherein the cognitive impairment is associated with narcolepsy, obstructive sleep apnea, shift work, Parkinson's disease, or attention deficit hyperactivity disorder.

17. The method of claim 10, wherein the subject is being treated with solriamfetol to improve wakefulness.

18. The method of claim 10, wherein the subject is a woman between the ages of 18 and 50 years.

* * * * *